US00PP28942P2

(12) United States Plant Patent
Jacobs

(10) Patent No.: US PP28,942 P2
(45) Date of Patent: Feb. 6, 2018

(54) ***CHRYSANTHEMUM* PLANT NAMED 'ZANMUPOP'**

(50) Latin Name: ***Chrysanthemum×morifolium* Ramat.**
Varietal Denomination: Zanmupop

(71) Applicant: Chrysanthemum Breeders Association Research BV, Valkenburg ZH (NL)

(72) Inventor: Henricus Cornelius Maria Jacobs, Valkenburg (NL)

(73) Assignee: Chrysanthenum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 15/530,242

(22) Filed: Dec. 16, 2016

(51) Int. Cl.
*A01H 5/02* (2006.01)

(52) U.S. Cl.
USPC ..... Plt./297

(58) Field of Classification Search
USPC ..... Plt./297
See application file for complete search history.

*Primary Examiner* — Annette H Para
(74) *Attorney, Agent, or Firm* — Steptoe & Johnson LLP

(57) ABSTRACT

A *chrysanthemum* plant named 'Zanmupop' characterized by its medium sized blooms with pink ray florets and prolific branching; natural season flowering date October 10; blooming for a period of 5 weeks.

3 Drawing Sheets

Botanical designation: *Chrysanthemum×morifolium* Ramat.

Cultivar denomination: 'Zanmupop'.

BACKGROUND OF THE INVENTION

The present invention relates to a new and distinct cultivar of *chrysanthemum* plant, botanically known as *Chrysanthemum×morifolium* Ramat., commercially known as a garden mum, and hereinafter referred to by the cultivar denomination 'Zanmupop'. 'Zanmupop' is a product of a breeding and selection program for outdoor pot mums (garden mums) which had the objective of creating new cultivars with a pink double type inflorescence, a natural season flowering date around October 10, blooming for a period of 5 weeks. 'Zanmupop' is a seedling resulting from a cross of the female parent 28284 (unpatented) with the male parent 45483 (unpatented). Plants of the new cultivar 'Zanmupop' differ from plants of the female parent in the following characteristics. (1) Presence disc florets. And (2) Natural season blooming date. (1) Disc florets are absent in the female parent, and present in the new plant. (2) Plants of the female parent flower one week later than those of the new plant. Plants of the new cultivar 'Zanmupop' differ from plants of the male parent in the following characteristics. (1) Ray floret color. And (2) Plant size. (1) Ray florets are purple in the male parent and pink in the new plant. (2) Plants of the male parent flower two weeks earlier than those of the new plant.

The new and distinct cultivar was discovered and selected as a flowering plant by Henricus Cornelius Maria Jacobs on a cultivated field in Rijsenhout, The Netherlands in week 41 2010. The first act of asexual production of 'Zanmupop' was accomplished when vegetative cuttings from the initial selection were propagated further in a controlled environment in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *chrysanthemum* (of about 19 weeks) is shown in the accompanying drawings, the color being as nearly true as possible with color photographs of this type.

DESCRIPTION OF THE INVENTION

Figure 1:
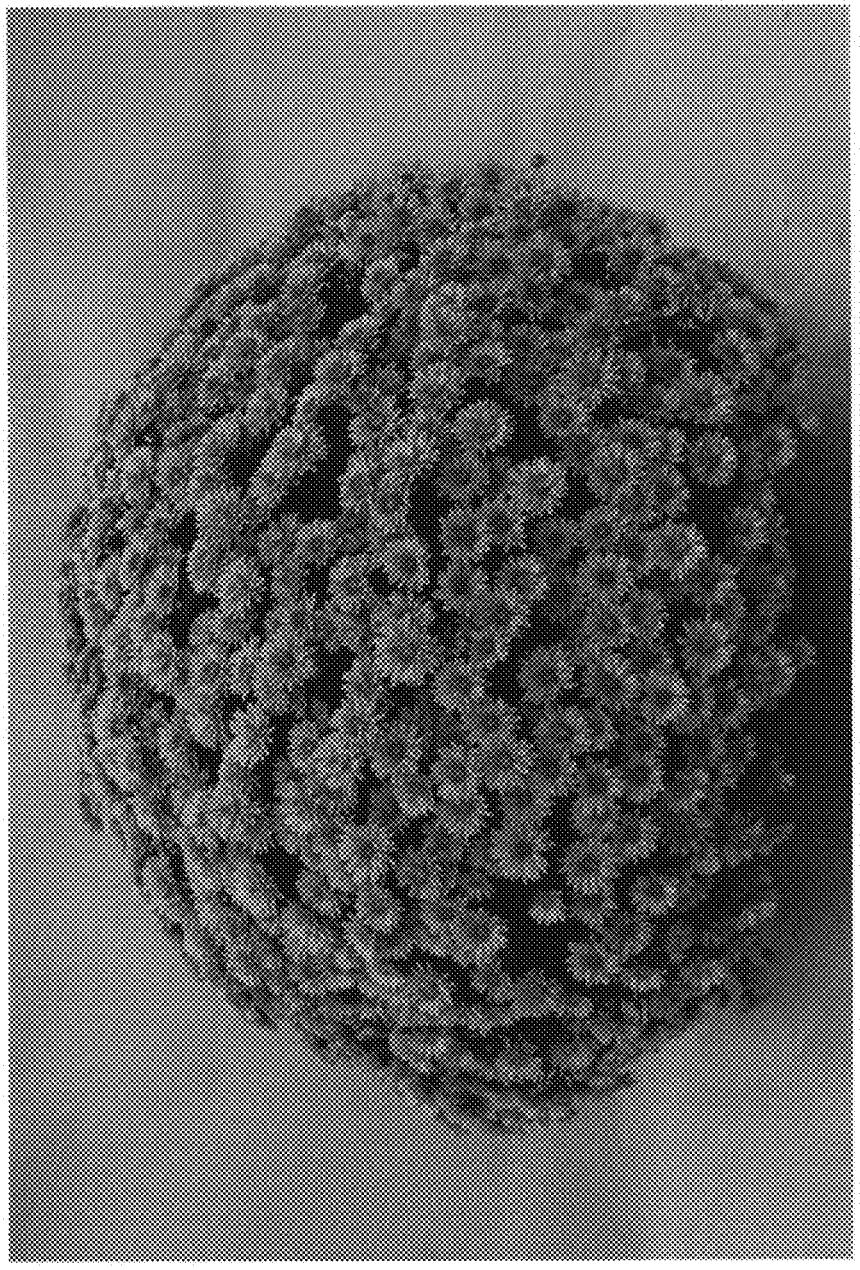
FIG. 1 shows a plant of the cultivar in full bloom.
Figure 2:
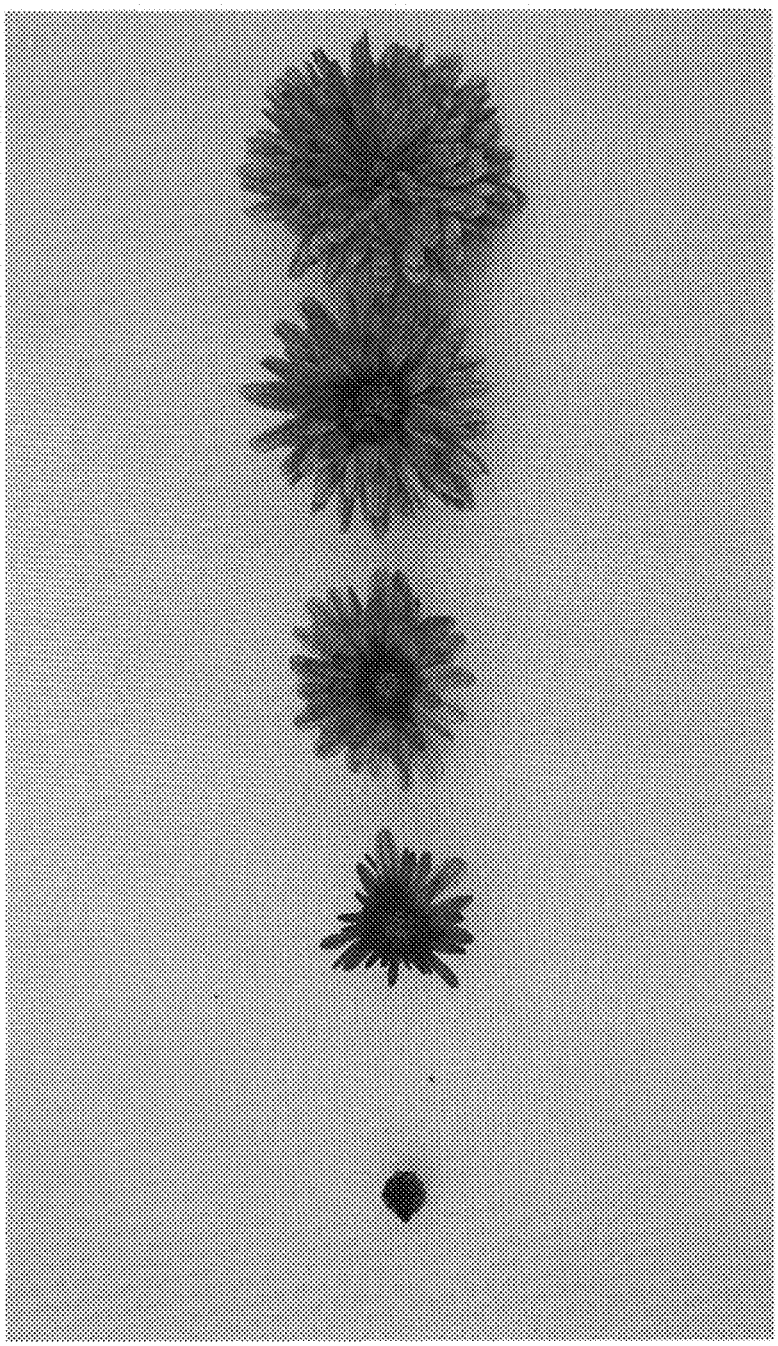
FIG. 2 shows the various stages of bloom of the new cultivar.
Figure 3:
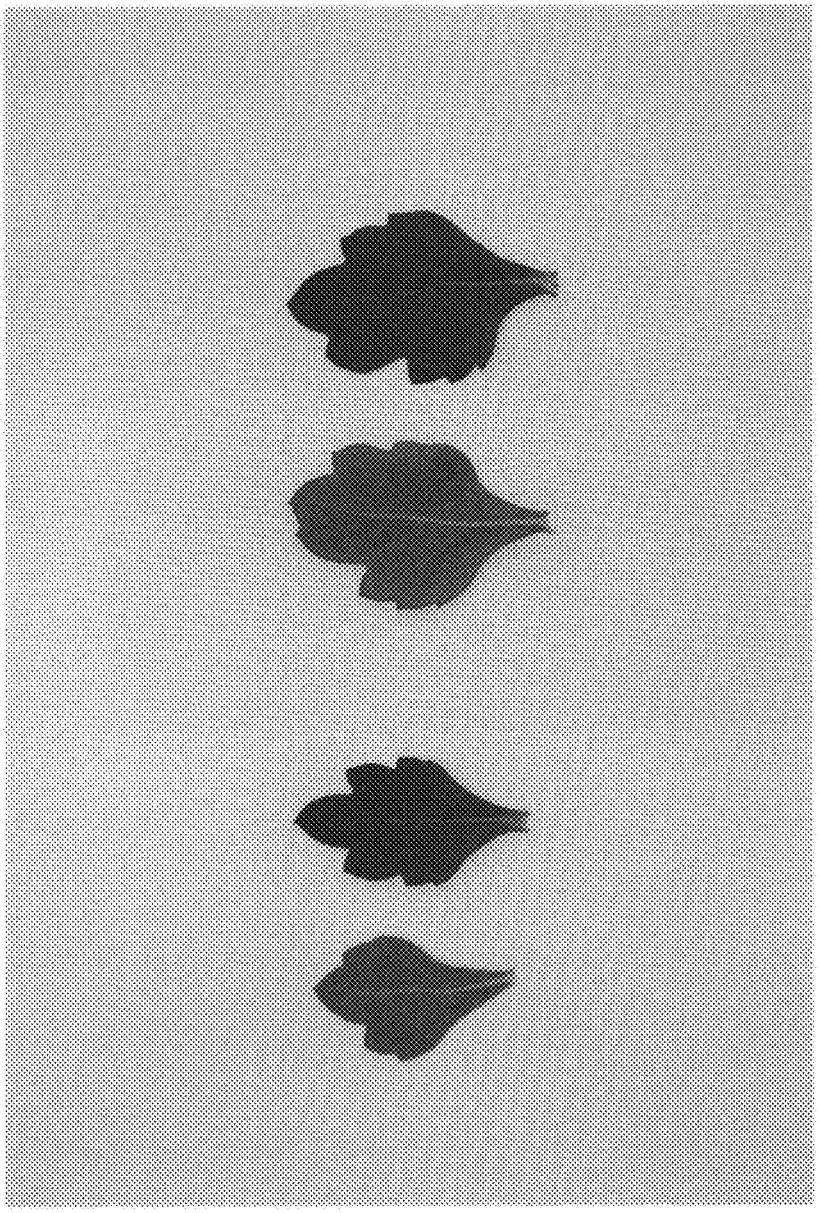
FIG. 3 shows the various stages of foliage of the new cultivar.

The observations and measurements were gathered from plants in the period of 17 to 23 weeks of age grown outdoor in Rijsenhout, the Netherlands, under natural day length and temperature and planted in week 23 in 2016, receiving drip irrigation. The natural blooming date of this crop was October 10. The average height of the plants was 37 cm. No growth retardants were used. No tests were done on disease or insect resistance or susceptibility. No tests were done on cold or drought tolerance. This new variety produces medium sized blooms with pink ray florets blooming for a period of 5 weeks.

From the cultivars known to the inventor the most similar existing cultivar in comparison to 'Zanmupop' is 'Zanmupizza' (U.S. Plant Pat. No. 26,511). When 'Zanmupizza' and 'Zanmupop' are being compared the following differences are noticed (1) Ray-floret color. And (2) Presence disc florets. (1) Ray-florets of 'Zanmupop' are more pink colored than those of 'Zanmupizza'. (2) Disc florets are present in 'Zanmupop' and lacking in 'Zanmupizza'.

The following is a description of the plant and characteristics that distinguish 'Zanmupop' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, sixth edition (2015).

TABLE 1

Botanical Description of *Chrysanthemum* × *morifolium* Ramat. 'Zanmupop'

| | |
|---|---|
| **Bud** | |
| Size: | Small; cross-section 3 mm, height 6 mm |
| Shape: | Round |
| Texture: | Pubescent |
| Outside color: | Greyed-green 191B |
| **Phyllaries** | |
| Number: | 25, arranged in 3 rows |
| Shape: | Elliptic |
| Apex: | Acute |
| Base: | Truncate |
| Margin: | Entire |
| Color: | Upper side: Green 143C<br>Lower side: Greyed-green 191B |
| Length and width: | 5 mm; 2 mm |
| Texture: | Pubescent |
| **Inflorescences** | |
| Type: | Double |
| Height: | 1.3 cm |
| Diameter: | 4 cm |
| Peduncle length: | 5-6.5 cm |
| Peduncle color: | Green N138B |
| Peduncle diameter: | 1.5 mm |
| Peduncle texture: | Pubescent |
| Number per branch: | About 6 inflorescences |
| Duration of flowering: | 5 weeks |
| Seeds: | Produced in small quantities, ovate, Greyed-brown 199A, length 1.5 mm, diameter 0.5 mm; texture: rough with ribs |
| Fragrance: | Faint chrysanthemum odor |
| **Color inflorescences** | |
| Center of inflorescence (disc florets): | Immature stage: Green-yellow 1D ; Mature stage: Green-yellow 1D |
| Color of upper side of ray florets: | Outer rows: Greyed-purple 186C to 186D; Inner Rows:Greyed-purple 186B |
| Color of lower side of ray florets: | Outer rows: Greyed-purple 186 C to 186D; Inner Rows: Greyed-purple 186B |
| Tonality from distance: | A garden mum with pink blooms and a purple center |
| Color of ray florets after aging of the plant: | Greyed-purple 186D |
| **Ray florets** | |
| Number of types: | 2 |
| Type: | Outer rows: Ligulate; Inner rows: Quilled |
| Texture: | Upper and lower side smooth |
| Number: | 170-180 |
| Shape: | Outer rows: Elliptic; Inner rows: Narrowly elliptic |
| Apex: | Outer rows: Dentate; Inner rows: Rounded |
| Base: | Attenuate |
| Cross-section: | Outer rows: Flat; Inner rows: Circular |
| Longitudinal axis: | Outer rows: Straight; Inner rows: Incurving |
| Length of corolla tube (outer rows): | 3 mm |
| Diameter corolla tube (outer rows): | 1 mm |
| Ray floret margin: | Entire |
| Ray floret length: | Outer rows: 2.5 cm: Inner rows: 1.2 cm |
| Ray-floret width: | Outer rows: 4 mm; Inner rows: 1.5 mm |
| Ratio length/width: | Medium (outer rows) to high (inner rows) |

TABLE 1-continued

Botanical Description of *Chrysanthemum* × *morifolium* Ramat. 'Zanmupop'

| | |
|---|---|
| **Disc florets** | |
| Disc diameter: | 2 mm |
| Distribution of disc florets: | Few, only visible in mature stage of inflorescences |
| Shape: | Tubular |
| Color: | Yellow-green 145C at base to Green Yellow 1D at apex |
| Length: | 3 mm |
| Diameter: | 1 mm |
| **Receptacle** | |
| Color: | Yellow-green 145D |
| Shape: | Domed raised |
| Height: | 5 mm |
| Diameter: | 7 mm |
| **Reproductive Organs** | |
| Androecium: | Present on only disc florets |
| Stamen length: | 3 mm |
| Stamen color: | Yellow-green 144A |
| Anther color: | Yellow 2A |
| Pollen: | Low amount |
| Pollen color: | Yellow 12A |
| Gynoecium: | Present on both ray and disc florets |
| Style color: | Yellow-green 154C |
| Style length: | 4 mm |
| Stigma color: | Yellow 7A |
| Stigma width: | 1 mm |
| Ovary: | Enclosed in calyx |
| Ovary color: | Yellow-green 149D |
| **Plant** | |
| Type: | Bushy |
| Growth habit: | Spherical shape |
| Growth rate: | Vigorous |
| Height: | 35-38 cm |
| Width: | 60-62 cm |
| Stem color: | Greyed-brown 199A |
| Stem strength: | Weak |
| Stem brittleness: | Brittle |
| Stem anthocyanin coloration: | Absent |
| Internode length: | 1-3 cm |
| Length of lateral branch: | From top to bottom 22 cm |
| Lateral branch color: | Green 138A |
| Lateral branch, attachment: | Weak |
| Lateral branch diameter: | 2 mm |
| Lateral branch, texture: | Pubescent with ribs |
| Branching (average number of lateral branches): | Dense with 8-9 breaks after pinching |
| Natural season blooming date: | October 10 (week 41) in Rijsenhout, the Netherlands |
| Roots—habits: | Fine, freely branching |
| Roots—color: | White 155A |
| **Foliage** | |
| Glossiness: | Leaf upper side: very weak<br>Leaf lower side: absent |
| Leaf color: | Upper side: Green 139A<br>Lower side: Green N138A |
| Color midvein: | Upper side: Yellow-green 147D<br>Lower side: Yellow-green 148D |
| Size: | Small; length 2.2-3 cm, width 1.5-2 cm |
| Quantity (number per lateral branches): | 22-24 |
| Shape: | Elliptic |
| Texture upper side: | Sparsely pubescent |
| Texture under side: | Pubescent |
| Venation arrangement: | Pinnate |
| Shape of margin: | Serrated |
| Shape of base of sinus between lateral lobes: | Rounded |

TABLE 1-continued

| Botanical Description of *Chrysanthemum* × *morifolium* Ramat. 'Zanmupop' | |
|---|---|
| Margin of sinus between lateral lobes: | Diverging |
| Shape of base: | Attenuate |
| Apex: | Mucronulate |
| Petiole strength: | Weak |
| Petiole attitude: | Moderately upwards |
| Petiole length: | 0.2 cm |
| Petiole diameter: | 2 mm |
| Petiole color: | Yellow-green 147D |
| Stipules: | Very small |

TABLE 2

| Differences with the comparison variety, when grown under identical conditions | | |
|---|---|---|
| | 'Zanmupop' | 'Zanmupizza' |
| Ray floret color | Greyed purple 186 B to 186D | Red-purple 72A |
| Disc florets | Present | Absent |

I claim:

1. A new and distinct *chrysanthemum* plant named 'Zanmupop' as described and illustrated.

* * * * *